(12) United States Patent
Shedlov et al.

(10) Patent No.: US 7,476,034 B2
(45) Date of Patent: Jan. 13, 2009

(54) DYNAMIC BUSHING FOR MEDICAL DEVICE TUBING

(75) Inventors: Matthew Shedlov, Rockford, MN (US); Kenneth Merdan, Greenfield, MN (US); Jeffrey P. Boodry, Shorewood, MN (US); Luke W. Lundquist, Rogers, MN (US); James K. Hitchcock, Forest Lake, MN (US); James M. Faucher, New Brighton, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1060 days.

(21) Appl. No.: 10/648,914

(22) Filed: Aug. 28, 2003
(Under 37 CFR 1.47)

(65) Prior Publication Data

US 2005/0049579 A1    Mar. 3, 2005

(51) Int. Cl.
*F16C 13/00* (2006.01)
*F16C 35/06* (2006.01)
*F16C 17/06* (2006.01)
*F16C 43/04* (2006.01)

(52) U.S. Cl. .................. 384/549; 384/129; 384/556
(58) Field of Classification Search .......... 384/510, 384/549, 557–559, 560, 584, 129, 556; 81/57.33, 81/57, 57.19, 53; 285/27
See application file for complete search history.

(56) References Cited

U.S. PATENT DOCUMENTS

| 2,399,446 | A | * | 4/1946 | Morgan, Jr. ............. 384/549 |
| 2,430,487 | A | * | 11/1947 | Wessenger ............. 384/549 |
| 3,251,589 | A | * | 5/1966 | Hofmann et al. ........ 384/549 |
| 3,302,496 | A | * | 2/1967 | Campbell et al. ........ 81/57.33 |
| 4,541,602 | A | * | 9/1985 | Potzas .................. 248/544 |
| 4,649,777 | A | * | 3/1987 | Buck .................... 81/57.19 |
| 4,811,635 | A | * | 3/1989 | Falgout, Sr. ............ 81/57.33 |
| 4,857,691 | A | | 8/1989 | Boatwright |
| 4,942,754 | A | * | 7/1990 | Patzelt .................. 72/247 |
| 5,073,694 | A | | 12/1991 | Tessier et al. |
| 5,345,057 | A | | 9/1994 | Muller |
| 5,421,955 | A | | 6/1995 | Lau et al. |
| D381,113 | S | * | 7/1997 | Safyan .................. D26/140 |
| 5,671,961 | A | * | 9/1997 | Buck .................... 294/116 |
| 5,703,340 | A | | 12/1997 | Ohta et al. |

(Continued)

FOREIGN PATENT DOCUMENTS

EP     0 842 729 A1     5/1998

(Continued)

OTHER PUBLICATIONS

Ostendor, "High Precision Laser Micro Machining" course, *Laser Institute of America*, Nov. 18, 1999, p. 7.

*Primary Examiner*—Marcus Charles
(74) *Attorney, Agent, or Firm*—Crompton, Seager & Tufte LLC

(57) ABSTRACT

A dynamic bushing and/or gripper mechanism comprises an apparatus for retaining a tubular member in a position during processing so that the tube does not move transverse to the longitudinal axis of the bushing, but wherein the tube may be rotated within the confines of the bushing and/or in the case of the gripper mechanism the tube may be moved longitudinally within the confines of the gripper.

15 Claims, 12 Drawing Sheets

U.S. PATENT DOCUMENTS

| | | | |
|---|---|---|---|
| 5,759,192 | A | 6/1998 | Saunders |
| 5,780,807 | A | 7/1998 | Saunders |
| 5,788,558 | A | 8/1998 | Klein |
| 5,852,277 | A | 12/1998 | Gustafson |
| 5,887,986 | A * | 3/1999 | Pouliquen et al. ........... 384/549 |
| 5,902,499 | A | 5/1999 | Richerzhagen |
| 5,904,075 | A * | 5/1999 | Buck ........................ 81/57.18 |
| 6,116,118 | A * | 9/2000 | Wesch, Jr. ................. 81/57.34 |
| 6,160,240 | A | 12/2000 | Momma et al. |
| 6,492,615 | B1 | 12/2002 | Flanagan |
| 6,684,737 | B1 * | 2/2004 | Schulze-Beckinghausen et al. ........................ 81/57.33 |

FOREIGN PATENT DOCUMENTS

| | | | |
|---|---|---|---|
| JP | 05119044 A * | 5/1993 | |
| JP | 2002154750 A * | 5/2002 | |
| SU | 560758 A1 * | 9/1977 | |
| SU | 1726726 A1 * | 4/1992 | |
| SU | 1819779 A1 * | 7/1993 | |
| WO | WO 89/03274 | 4/1989 | |
| WO | WO 99/56907 | 11/1999 | |
| WO | WO 00/64374 | 11/2000 | |
| WO | WO 01/66036 A2 | 9/2001 | |
| WO | WO 03/000157 A1 | 1/2003 | |

\* cited by examiner

DYNAMIC BUSHING FOR MEDICAL DEVICE TUBING

CROSS-REFERENCE TO RELATED APPLICATIONS

Not Applicable

STATEMENT REGARDING FEDERALLY SPONSORED RESEARCH

Not Applicable

BACKGROUND OF THE INVENTION

A stent is a radially expandable endoprosthesis which is adapted to be implanted in a body lumen. Stents are typically used in the treatment of atherosclerotic stenosis in blood vessels and the like to reinforce body vessels and to prevent restenosis following angioplasty in the vascular system. They have also been implanted in urinary tracts, bile ducts and other bodily lumen. They may be self-expanding or expanded by an internal radial force, such as when mounted on a balloon.

Delivery and implantation of a stent is accomplished by disposing the stent about a distal portion of the catheter, percutaneously inserting the distal portion of the catheter in a bodily vessel, advancing the catheter in the bodily lumen to a desired location, expanding the stent and removing the catheter from the lumen. In the case of a balloon expandable stent, the stent is mounted about a balloon disposed on the catheter and expanded by inflating the balloon. The balloon may then be deflated and the catheter withdrawn. In the case of a self-expanding stent, the stent may be held in place on the catheter via a retractable sheath. When the stent is in a desired bodily location, the sheath may be withdrawn allowing the stent to self-expand.

In the past, stents have been generally tubular but have been composed of many configurations and have been made of many materials, including metals and plastic. Ordinary metals such as stainless steel have been used as have shape memory metals such as Nitinol and the like. Stents have also been made of bio-absorbable plastic materials. Stents have been formed from wire, tube stock, etc. Stents have also been made from sheets of material which are rolled.

A number of techniques have been suggested for the fabrication of stents from sheets and tubes. One such technique involves laser cutting a pattern into a sheet of material and rolling the sheet into a tube or directly laser cutting the desired pattern into a tube. Other techniques involve cutting a desired pattern into a sheet or a tube via chemical etching or electrical discharge machining.

Laser cutting of stents has been described in a number of publications including U.S. Pat. No. 5,780,807 to Saunders, U.S. Pat. No. 5,922,005 to Richter and U.S. Pat. No. 5,906,759 to Richter. Other references wherein laser cutting of stents is described include: U.S. Pat. No. 5,514,154, U.S. Pat. No. 5,759,192, U.S. Pat. No. 6,131,266 and U.S. Pat. No. 6,197,048.

Past laser cutting systems typically mount the tube to be cut from a spindle shaft or other rotary assembly wherein the laser is mounted perpendicular to the longitudinal axis of the tube. To maintain the position of the tube relative to the laser during the cutting process, the tube is typically guided through a rigid or fixed bushing which constrains the tube from moving transverse to the longitudinal axis of the tube. However, if the tube has any outer diameter variations the tube will be capable of slight movement within the bushing and potentially move in and out of focus of the laser resulting in improper cutting of the tube. Current bushing designs are very operator dependent and do not allow for any tubing variability and are thus difficult and time consuming to use and maintain.

In light of the above a need exists to provide a more dynamic bushing with is capable of maintaining the position of the tube, while being able to accommodate a wide variety of tube diameters and surface features without requiring extensive modification or manually sizing of the bushing for every tube used therewith.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

The present invention is directed to a variety of embodiments. In at least one embodiment the invention is directed to a system for cutting, etching and/or otherwise processing a hollow metal tube for manufacturing a stent. In some embodiments the tube is engaged to a rotary assembly for rotating the tube relative to a laser or other processing tool. In order to prevent the tube from moving transverse to the longitudinal axis of the tube the tube is passed through a dynamic bushing. A dynamic bushing may be embodied in a variety of forms. For example:

In at least one embodiment a dynamic bushing comprises a top dead center guide and at least two bottom guides, wherein the at least two bottom guides are adjustably positioned relative to the to dead center guide to define a variable tube retention area. In some embodiments the bottom guides are positioned apart on a piston or other moveable member. A pressure regulator, servo proportional regulator, a biasing assembly or other device may be used to push the piston and thus the bottom guides toward the top dead center guide. In this manner a wide range of tube diameters may be held within the tube retention area without creating an undesirable amount of friction between the external surface of the tube and the various guides. In at least one embodiment one or more of the guides comprise independently adjustable rolling balls which individually contact the tube at single point. In some embodiments one or more of the guides comprise adjustable leaf springs.

In at least one embodiment a dynamic bushing comprises a grove in which a tube to be processed is positioned. In some embodiments the groove is substantially V-shaped so as to contact the tube along only two lines or regions of contact. An adjustable arm or other member applies an adjustable force to the tube from the exposed 'top' of the groove, to provide a third line or region of contact. Where the bushing and rotary assembly are configured to process the tube in a horizontal configuration the amount of force applied by the arm to the tube may be varied depending on the weight of the arm or a ballast attached thereto. In a vertical stent processing application such as is described in co-pending U.S. patent application Ser. No. 10/190,975, filed Jul. 8, 2002, the arm may retain the tube within the groove by utilizing a compression spring, pneumatic or hydraulic cylinder, or other device to vary the force directed to the tube by the arm. In some embodiments the dimensions of the groove may be varied. In some embodiments the groove and/or arm defines one or more fluid holes through which a coolant or other fluid may be passed to create a positive pressure to prevent debris from entering the tooling.

In at least one embodiment the dynamic bushing comprises a hydraulic chamber into which at least a portion of the tube is guided. Fluid is injected into the chamber from one or more injection ports. A gland plate is positioned adjacent to the ends of the chamber in order to regulate pressure and limit release of fluid from the chamber. When fluid is injected into the chamber when a, tube is positioned therein, the chamber acts as a hydraulic bearing as long as the fluid supplied to the chamber exceeds the fluid lost through the gland plates. In some embodiments one or both gland plates define a labyrinth to create pressure decreasing zones to minimize loss of fluid from the chamber. In use the chamber provides a uniform pressure equally to all surfaces of the tube thus providing a highly accurate centering function.

In at least one embodiment of the invention a processing system may comprise a gripper mechanism. In some embodiments the gripper mechanism comprises a pneumatically actuated gripper having two jaws that are moveable between a release position and a gripping position. In some embodiments the gripper is mounted on a low friction pivot for self-alignment of the gripper relative to the tubing to be processed. In some embodiments a processing system comprises a dynamic bushing and a gripper mechanism.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

Figure 1:
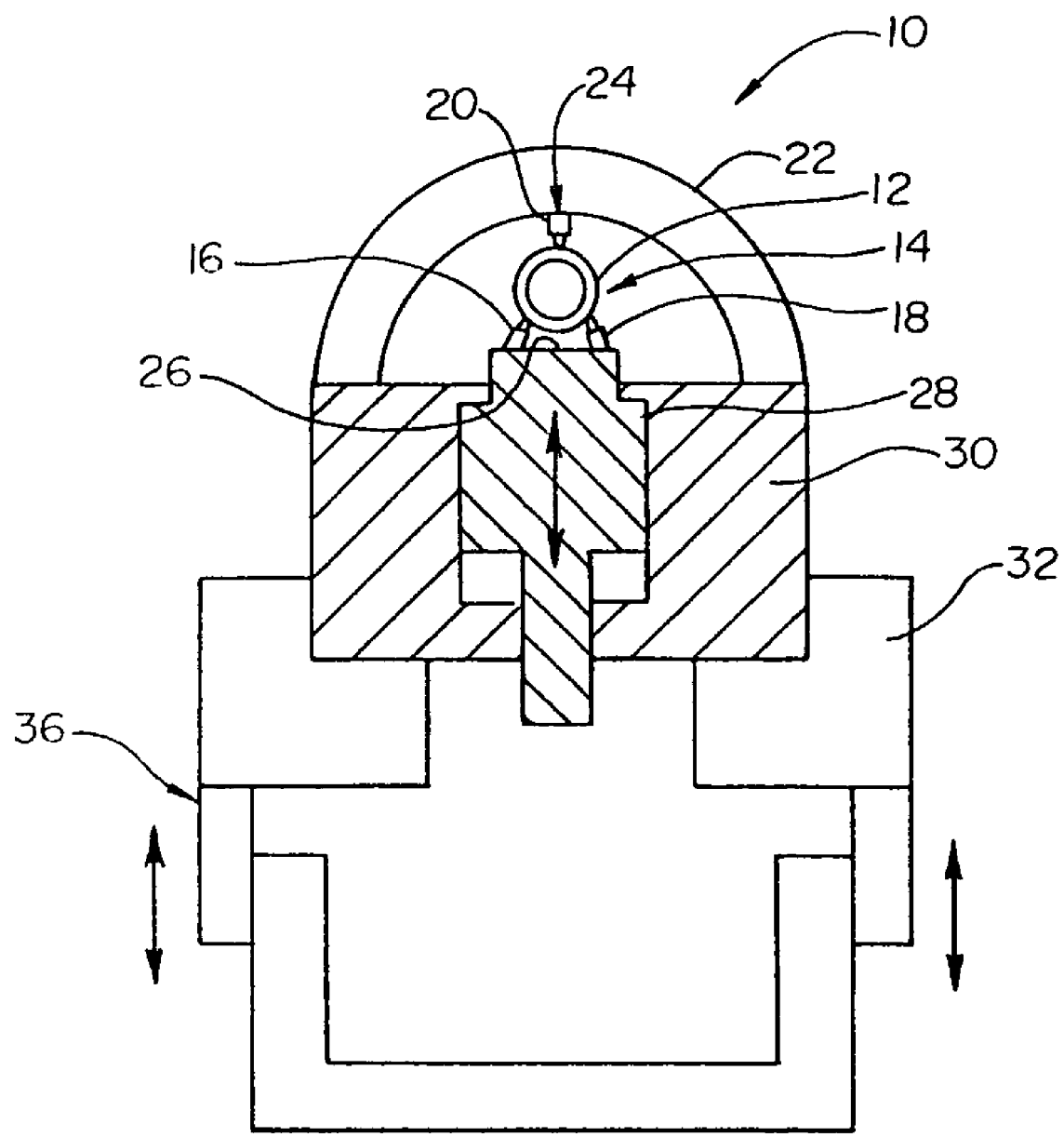
FIG. 1 is a side view of an embodiment of the invention.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

As indicated above the present invention is directed to a variety of embodiments. In at least one embodiment, shown in FIG. 1, the invention is directed to a dynamic bushing assembly (assembly), indicated generally at 10, for constraining the tube 12 when an end of the tube 12 is engaged to a tubular member cutting system or rotary assembly 200, such as the example shown in FIG. 11, for use in processing the tube into a stent or other device.

In the embodiment shown in FIG. 1, a portion of the tube 12 is passed through and positioned within a tube retention area 14. The retention area 14 is defined by at least two bottom guides 16 and 18 and at least one top or center guide 20. One or more of the guides 16, 18 and 20 are adjustable in position relative to the others to allow the effective diameter of the retention area 14 to be expanded or contracted as desired depending on the diameter of the outer surface 15 and/or other external surface characteristics of the tube 12.

In at least one embodiment the top guide 20 is statically mounted to a crown 22. Crown 22 may be any type of structure or member suitable for maintaining the top guide 20 in a stable position during processing of the tube 12. In at least one embodiment, such as in the example shown, the crown 22 is a substantially U-shaped member with the top guide engaged to the crown at the internal apex 24 of the crown 22.

In order to provide a retention area 14 which is of an appropriate shape to receive a tube 12 the bottom members are positioned on a substantially concave platform 26. Platform 26 defines a surface of a piston 28 which may be adjustably positioned relative to the crown 22, thereby providing a mechanism for moving the guides 16 and 18 relative to the top guide 20. Thus by moving the piston 28 and the associated guides 16 and 18 away from the top guide 20 the retention area may be enlarged, and by moving the piston 28 toward the top guide 20 the size of the retention area 14 is reduced.

To provide the assembly 10 with improved stability, the piston 28 is positioned within a piston housing 30 which prevents the piston 28 from moving lateral to the tube 12 regardless of the position of the piston 28 relative to the top guide 20. The housing 30 is mounted to and at least partially contained within a cradle 32 which may be moveably or fixedly engaged to a floor or other surface upon which the assembly 10 rests. In some embodiments the cradle 32 is engaged to a base 34 having an elevator mechanism 36 which allows the cradle 32 and components supported thereby to be vertically repositioned as desired.

Figure 2:
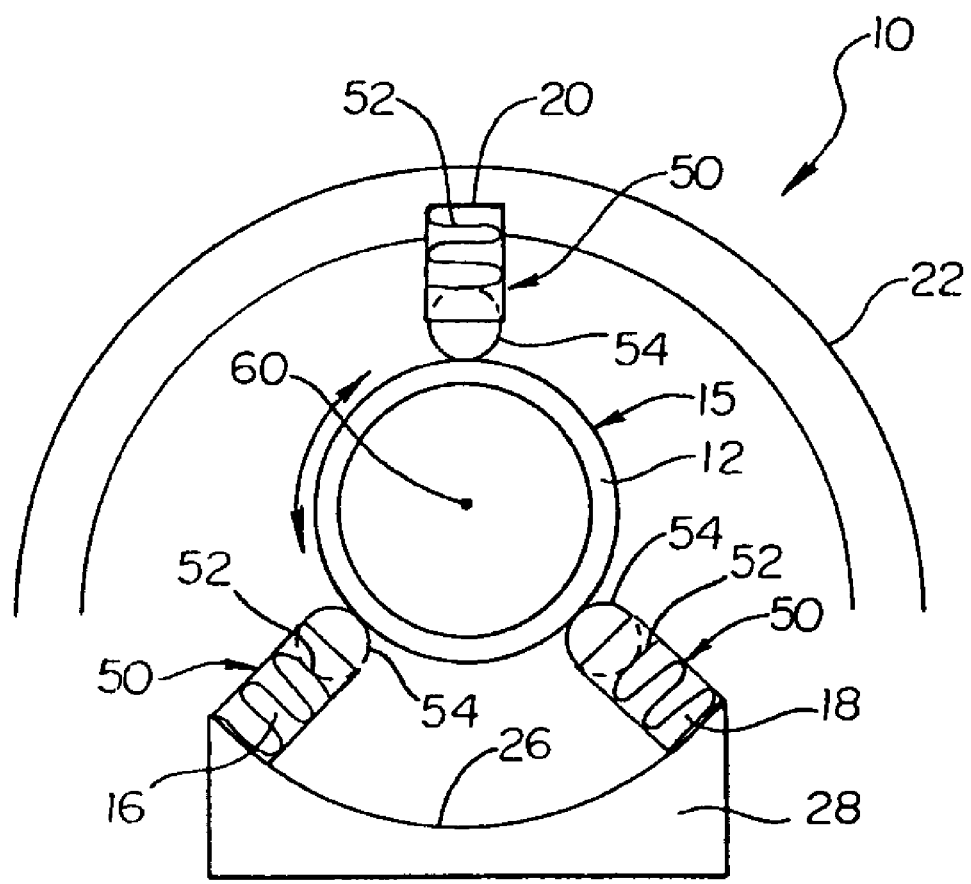
FIG. 2 is a close-up side view of the retention area of the embodiment shown in FIG. 1 wherein a tube is engaged therein.

As is shown in FIG. 2, a tube 12 is retained within the retention area 14, when the piston 28 is moved adjacent to the top guide 20 so that the outer surface 15 of the tube 12 is in contact with all three guides 16, 18 and 20.

In some embodiments at least guides 16 and 18 may be independently moveably adjustable relative to each other along the platform 26.

Figure 3:
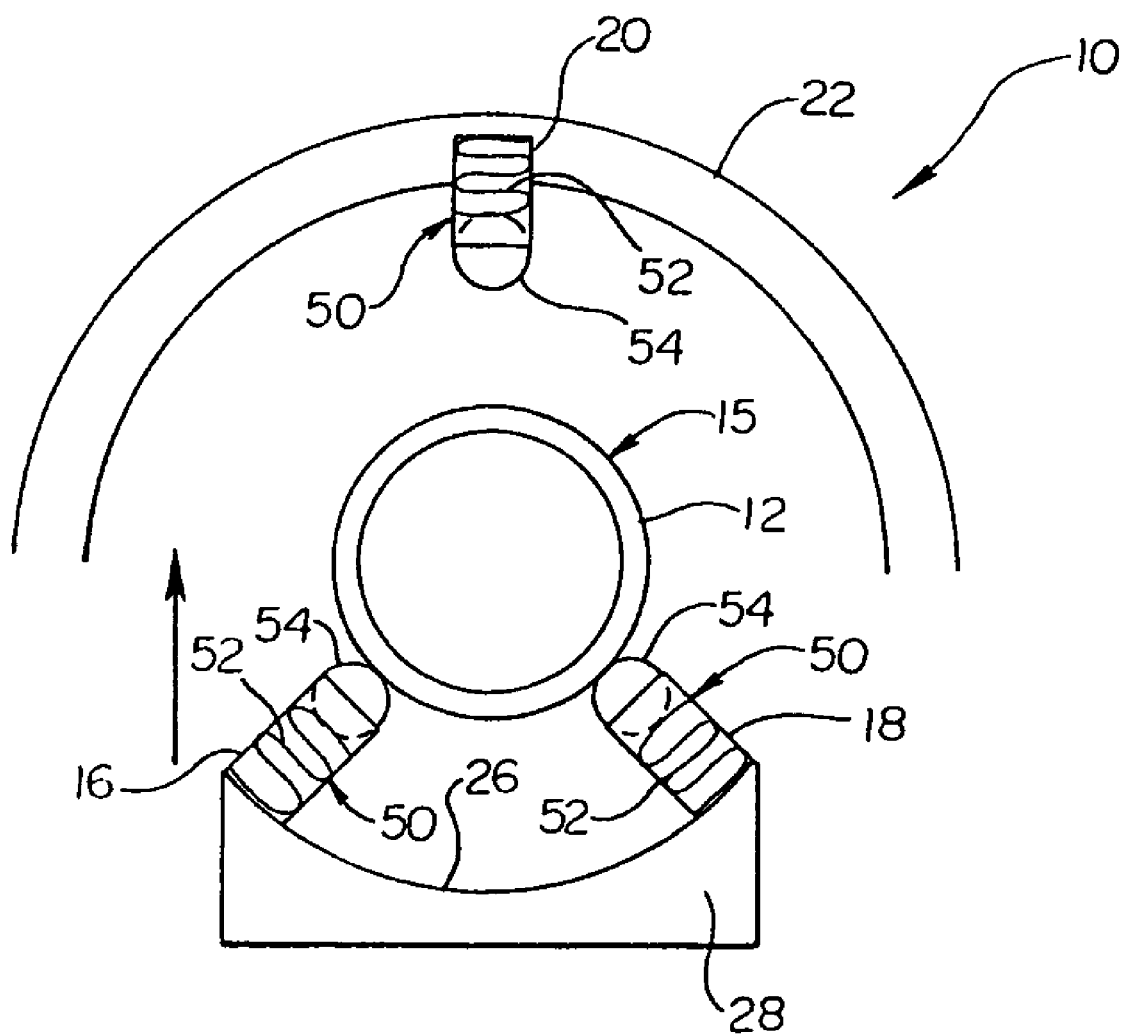
FIG. 3 is a close-up side view of the retention area of the embodiment shown in FIG. 1 wherein the tube is not fully engaged therein.

In the embodiment shown in FIGS. 2 and 3 the guides 16, 18 and 20 are defined by a guide housing 50 which contains a biasing mechanism 52. The biasing mechanism 52 biases a bearing or roller ball 54 in an outward direction away from the housing 50. By moving the guides 16, 18 toward the top guide 20 the roller balls 54 of each guide 16, 18 and 20 contact the outer surface 15 of the tube 12 at a single point respectively. The roller balls 54 of each guide are freely rotatable within the housings 50, as a result, when the roller balls 54 contact the tube 12, the tube 12 is able to be rotated about a longitudinal axis 60, but remains restrained from moving transverse to the longitudinal axis 60 about which the tube is disposed such as is shown in FIG. 2.

In order to prevent excess wear on the roller balls 54, in some embodiments the balls 54 are at least partially constructed from or coated with a ceramic, crucible powder metal, tungsten carbide, and/or other hard wear resistant material.

The biasing mechanism 52 within each housing 50 may be any type of mechanism which expresses a K-factor or biasing force, such as for example a spring, a pressurized fluid column, hydraulic mechanism, etc. The K-factor or amount of biasing force of each guide 16, 18 and 20 may be independently adjusted as desired. In at least one embodiment the K-factor expressed by the top guide 20 is greater than that of the bottom guides 16 and 18.

Figure 4:
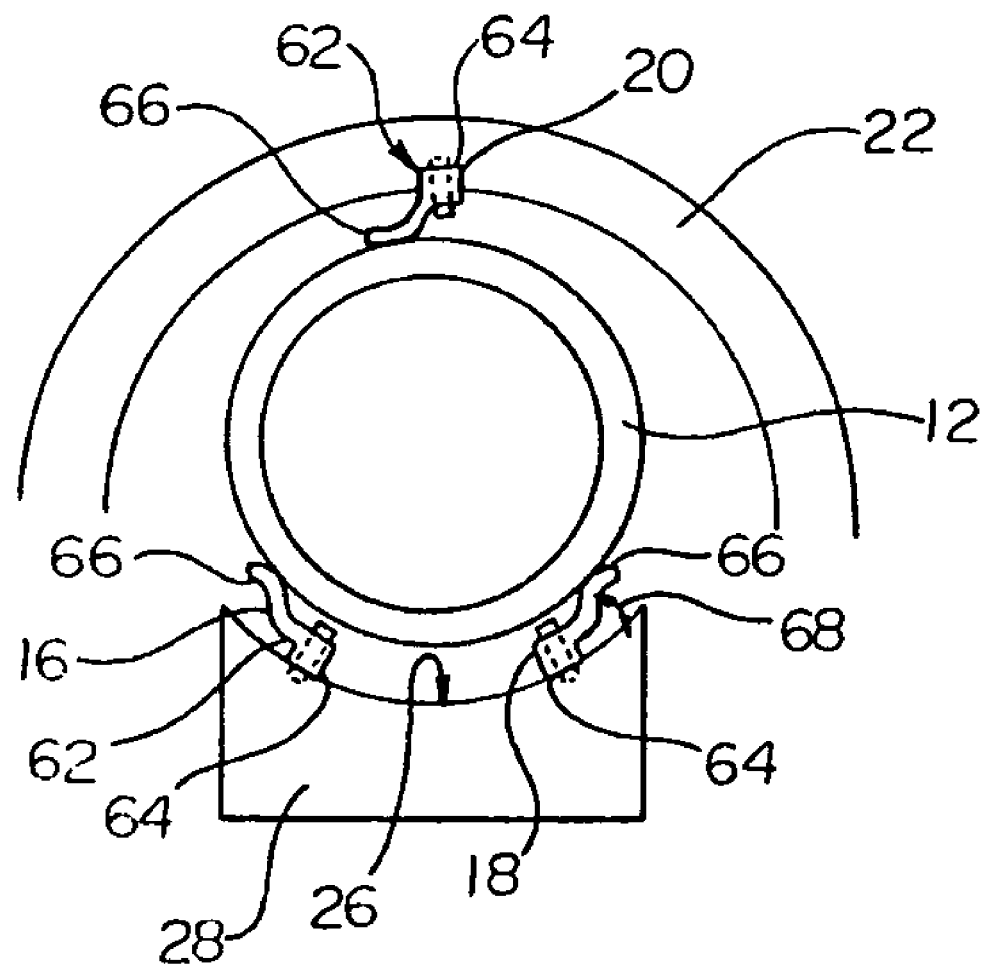
FIG. 4 is a cross-sectional view of an example of a guide mechanism suitable for use in the embodiment shown in FIG. 1.

In an alternative embodiment of the guides shown in FIGS. 2 and 3, one or more of the guides 16, 18 and 20 may comprise a leaf spring 62 such as is shown in FIG. 4. In the case of the bottom guides 16 and 18, a first end 64 of each leaf spring 62 is adjustably engaged to the platform 26 of piston 28. The second end 66 of the leaf spring 62 extends outwardly away from the first end 64 to define an adjustable biasing angle 68. The second end 66 of each leaf spring 62 is designed to tangentially contact the tube 12 when the piston is moved into position to secure the tube 12 within the retention area 14. In the case of the top guide 20 the first end 64 of the leaf spring is adjustably engaged to the crown 22.

Figure 5:
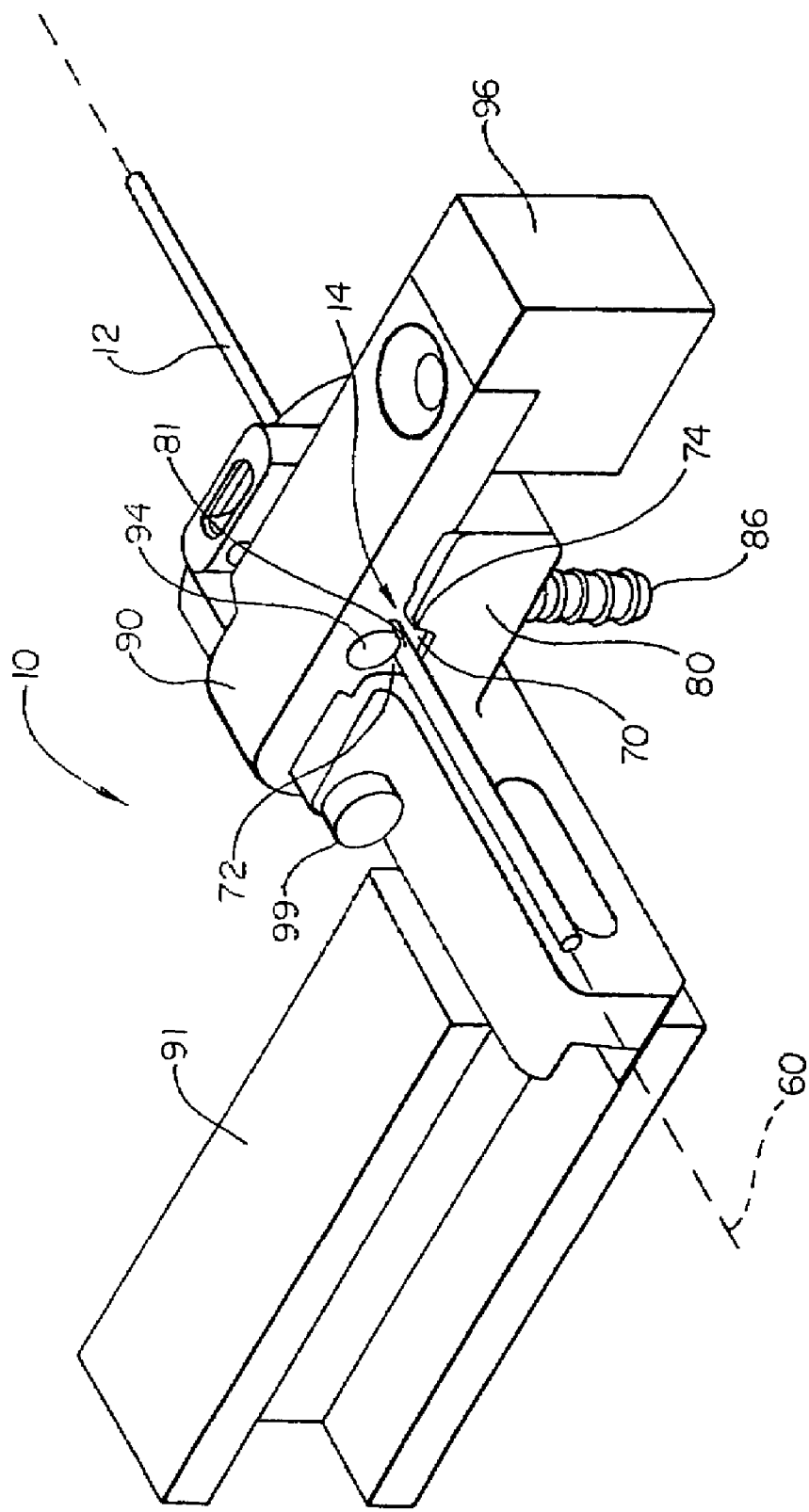
FIG. 5 is a perspective view of an embodiment of the invention.
Figure 6:
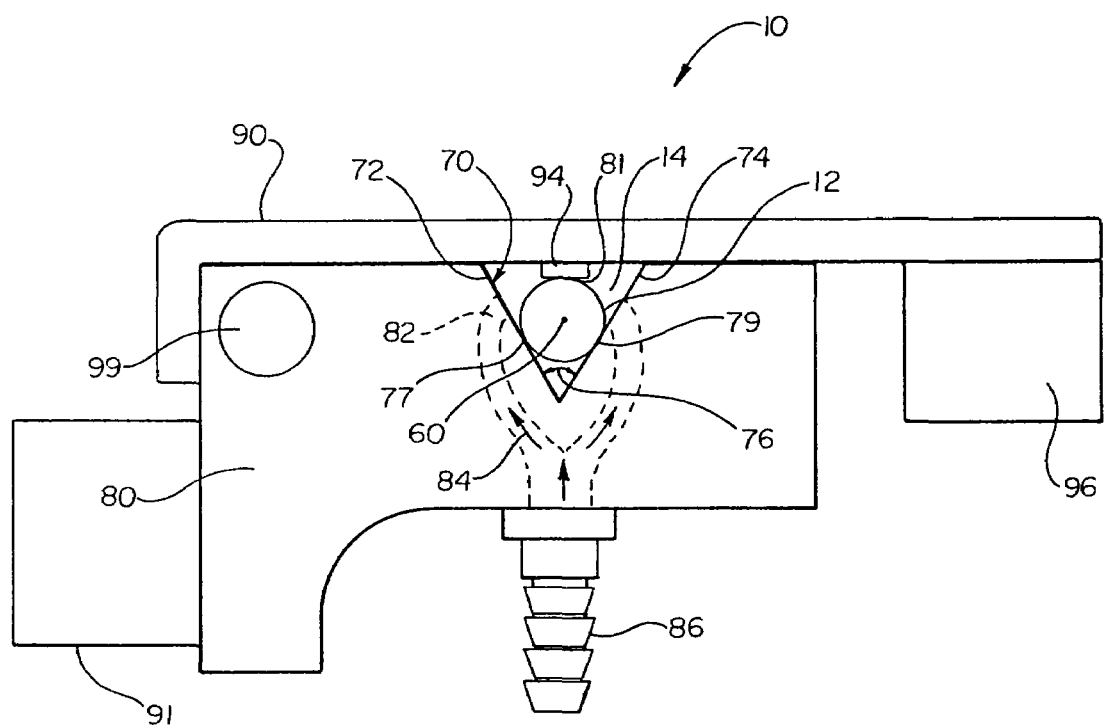
FIG. 6 is a cross-sectional side view of the embodiment shown in FIG. 5

An alternative embodiment of the invention is shown in FIGS. 5-8, wherein a the assembly 10 is comprised of a base block 80 which partially defines a substantially V-shaped tube retention area 14 within which tube 12 is retained during a stent cutting process. Retention area 14, is defined on two sides by V-groove 70 portion of the base block 80. As is best shown in FIG. 6, the V-groove 70 comprises two sides 72 and 74 which form an angle 76 greater than 0 degrees but less than 180 degrees. In at least one embodiment the angle 76 is between about 45 degrees and about 135 degrees.

In some embodiments the angle 76 and thus the distance between sides 72 and 74 may be varied to accommodate a wide variety of tube outer diameters. However, even in an embodiment where the angle 76 is fixed a wide range of tube diameters may be accommodated within the V-groove 70. A tube 12 is retained within the V-groove 70 by engaging each side 72 and 74 of the groove at a tangential point or line of contact 77 and 79 which is substantially parallel to the longitudinal axis 60 about which the tube 12 is mounted. Depending on the outer diameter of the tube 12 the position of the lines of contact 77 and 79 relative to the sides 72 and 74 will vary. Only if the tube 12 has an outer diameter greater than the widest distance between sides 72 and 74 would it be necessary to enlarge the angle 76 to increase the distance between sides 72 and 74.

To prevent wear and minimize friction, the sides 72 and 74 are at least partially constructed from a material having a hardness of at least 64 as measured on the Rockwell-C hardness scale. In at least one embodiment the V-groove 70 is a carbide insert within the base block 80.

The sides 72 and 74 may be wire burned, polished and/or coated with a material such as titanium nitrate or other hardening agent(s). A hardening agent may be applied to the sides 72 and 74 by vapor deposition or other desired method. In some embodiments sides 72 and 74 are coated with a lubricant.

Figure 8:
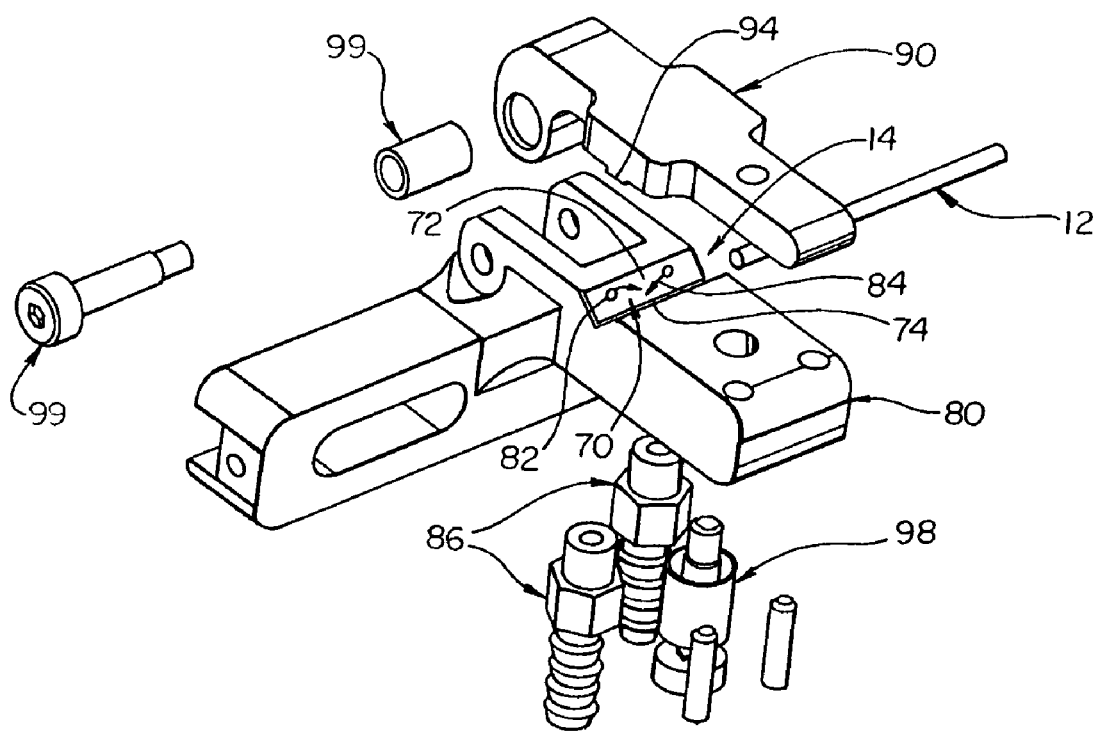
FIG. 8 is an exploded view of the embodiment shown in FIG. 7.

As is shown in FIGS. 6 and 8, in some embodiments the sides 72 and 74 define one or more coolant ports 82 through which a coolant, indicted by arrows 84 may be injected into the retention area 14. The coolant 84 creates a positive pressure within the retention area 14 to prevent slag and other debris from entering the assembly 10. Ports 82 pass through the block 80 and are in fluid communication with one or more fittings 86. Fittings 86 are in turn in fluid communication with a fluid source (not shown). Fluid or coolant 84 may be injected into, as well as removed, from the V-groove 70 by the one or more fittings 86.

Figure 7:
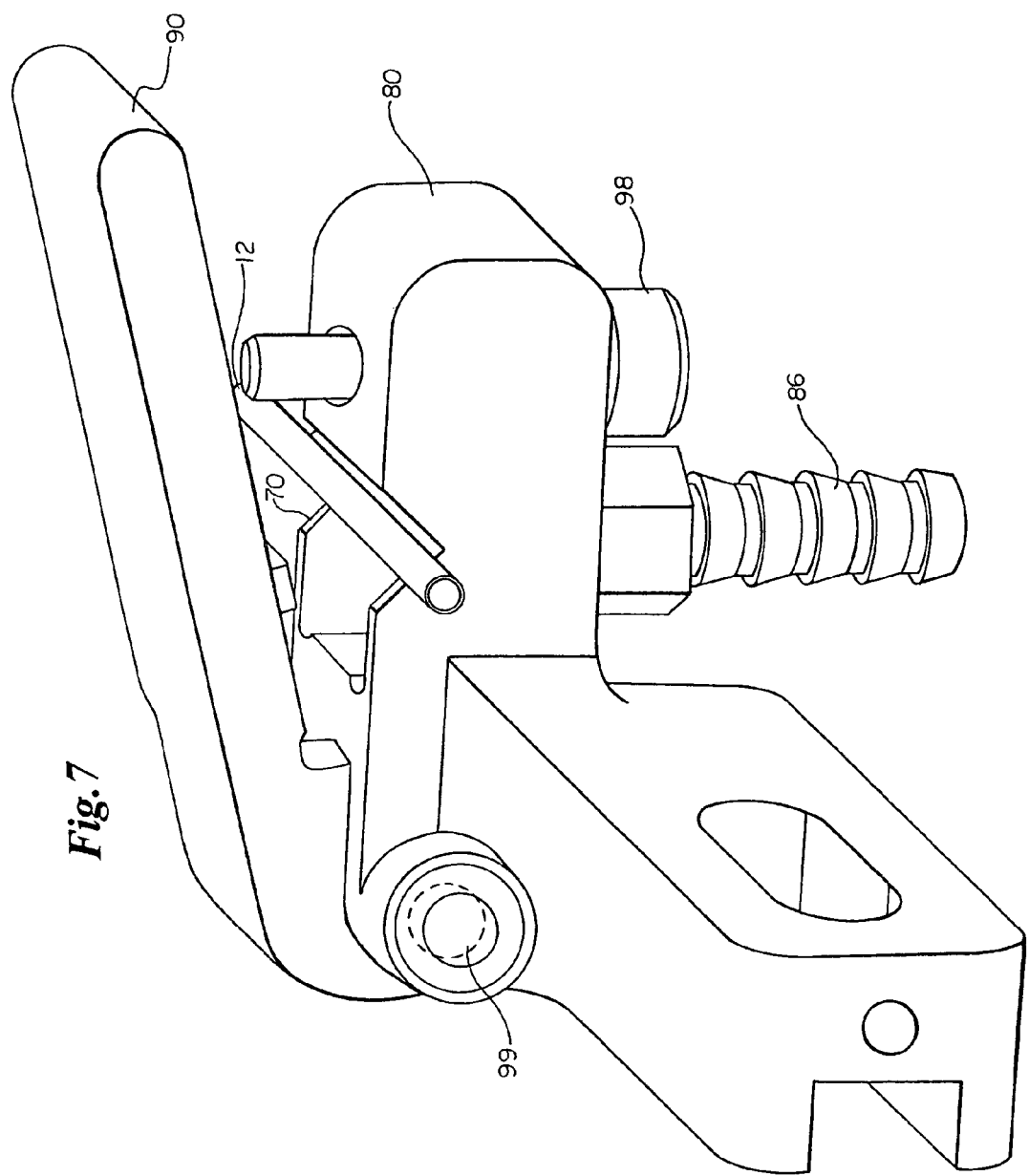
FIG. 7 is a perspective view of an embodiment of the invention similar to that shown in FIG. 5, wherein the top plate or arm in the open position and the ballast is replaced with a compression spring assembly.

In order to secure the tube 12 within the V-groove 70 a top plate or arm 90 is pivotally mounted to the base block 80 at a pivot hinge 99. As illustrated in FIG. 8, pivot hinge 99 may be a nut and bolt assembly, a dowel, or any other retaining mechanism which provides the arm 90 the ability to be pivotally engaged to the block 80. The arm 90 is moveable between an open position wherein the V-groove is open or uncovered such as is shown in FIG. 7, and a closed position, shown in FIGS. 5 and 6, wherein the arm 90 overlays the V-groove 70 and tangentially contacts the tube 12 at a top point or line of contact 81.

As best shown in FIG. 6 by closing the arm 90 over the V-groove 70, a tube contained within the retention area 14 will be tangentially engaged along three lines of contact 77, 79 and 81. The arm 90 may comprise a contact member 94 which is in contact with the tube 12 to form the top line of contact 81. Like the sides 72 and 74 of the V-groove 70, in some embodiments the contact member 94 is a carbide insert or other material having a hardness of at least 64 as measured on the Rockwell-C hardness scale.

The contact member 94 may be wire burned, polished and/or coated with a material such as tin, titanium nitrate, or other hardening agent. A hardening agent may be applied to the contact member 94 by vapor deposition or other desired method. In some embodiments contact member 94 is coated with a lubricant.

In some embodiments such as is shown in FIG. 5, the contact member 94 is substantially cylindrically shaped. The contact member 94 may be freely rotatable relative to the arm 90 and the tube 12 to reduce wear on the tube 12 during rotation thereof. Alternatively, the contact member 94 may be a flat planar surface, a point or edge or may be any other shape desired. In some embodiments the contact member 94 may comprise a polyethylene insert.

In the embodiments shown in FIGS. 5 and 6, arm 90 is held in the closed position over the tube 12 simply as a result of the orientation of the assembly 10 which allows gravity to pull the arm down. If necessary or desired the arm may comprise a ballast member 96 which provides additional weight to the arm 90 to ensure the arm remains securely in position over the V-groove 70. Ballast member 96 may have a weight of zero to about ½ of a pound (8 oz., 227 grams). In some embodiments the ballast member 96 weighs about ¼ of a pound (4 oz., 113 grams) to about ⅜ of a pound (6 oz. 170 grams).

In the embodiments shown in FIGS. 7 and 8, a compression spring, air cylinder or other biasing mechanism 98 may be utilized to retain the arm 90 in the closed position, rather than a ballast member or gravity alone. A biasing mechanism 98 may be utilized to vary the amount of downward force applied to the tube 12 when the arm is in the closed position.

Figure 9:
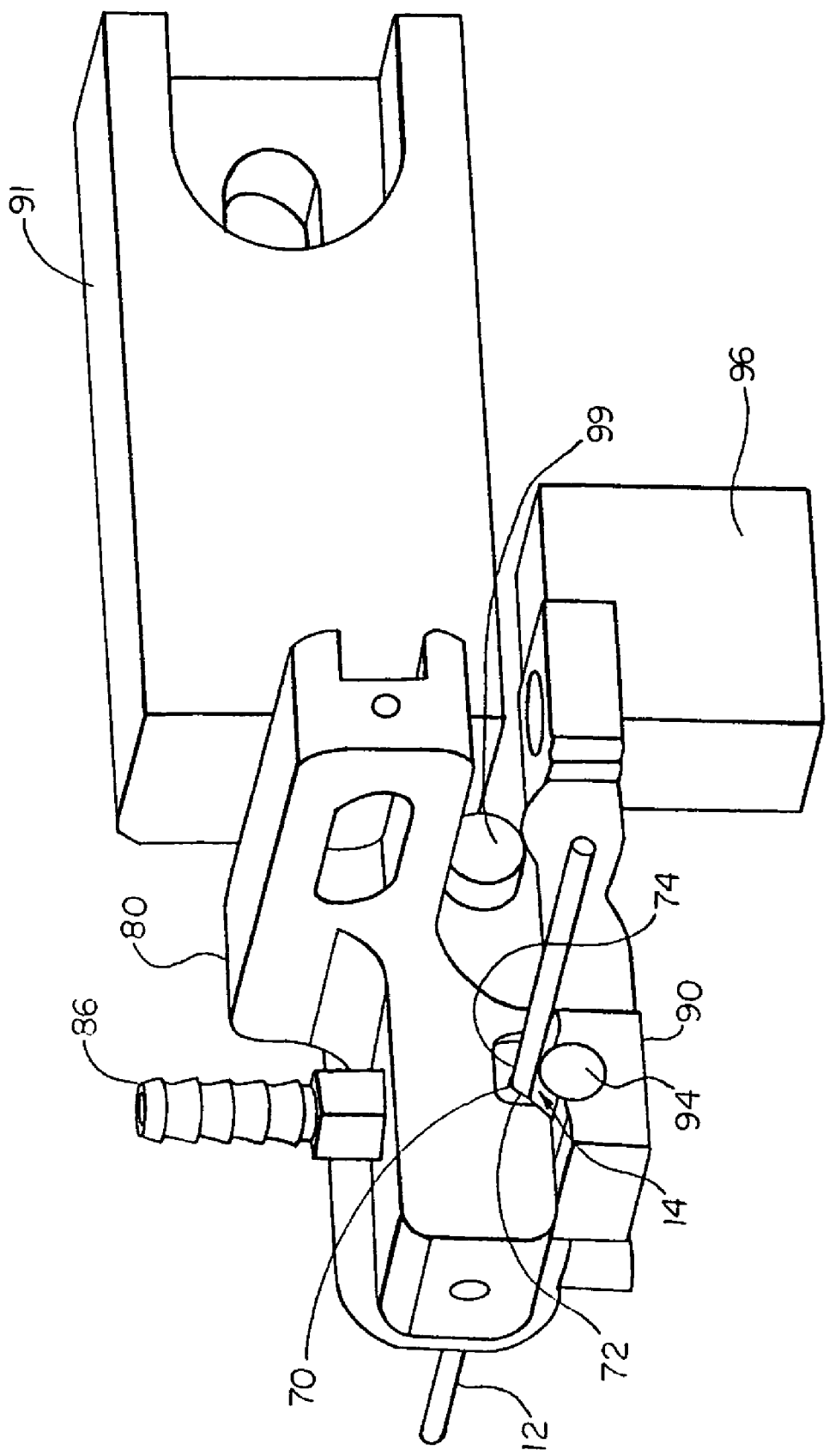
FIG. 9 is a perspective view of an embodiment of the invention.

If desired the assembly 10, such as is shown and described in FIGS. 5 and 6 may be inverted, as is shown in FIG. 9, so that the tube 12 tends to fall away from the sides 72 and 74 of the V-groove 70 unless the arm 90 is held in the closed position. In such an inverted embodiment, such as is shown in FIG. 9 the arm 90 is reconfigured to mount the ballast member 96 on an opposing end of the arm than in the embodiments of FIGS. 5 and 6. Repositioning the ballast member 96 has the affect of allowing the arm 90 to be biased in an upward direction against the tube 12.

In the various embodiments shown in FIGS. 5-6 and 9 the assembly 10 may be mounted or otherwise engaged directly to an existing rotary assembly (not shown) using a mounting arm 91. Mounting arm 91 may have any shape or configuration to allow the assembly 10 to allow the tube 12 to extend from the rotary assembly through the dynamic bushing assembly 10 along a common longitudinal axis 60.

Figure 10:
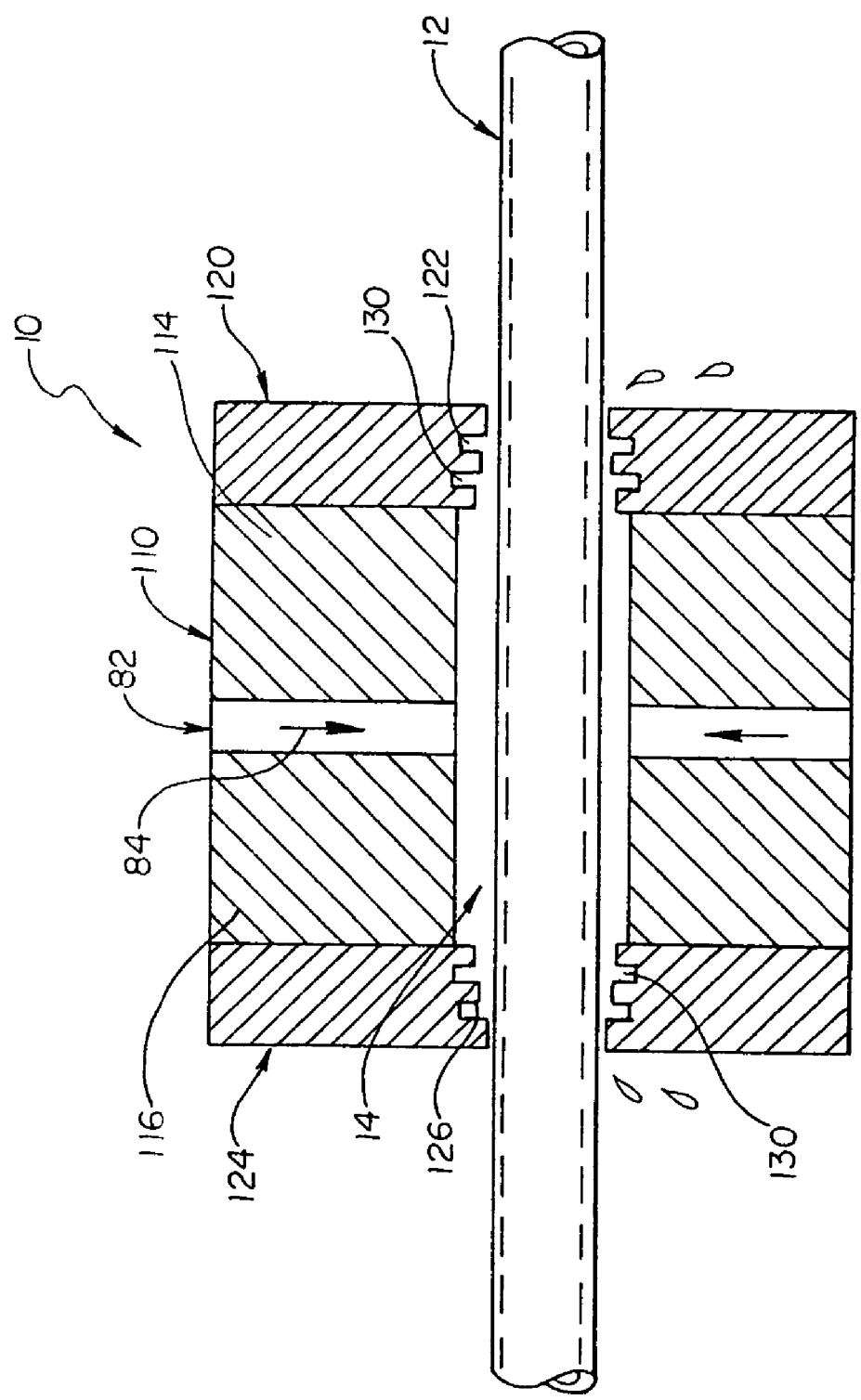
FIG. 10 is a longitudinal cross-sectional view of an embodiment of the invention.

In yet another embodiment of the invention, an example of which is shown in FIG. 10, the assembly 10 may comprise a tooling block 110 which defines a retaining area 14 in which a portion of the tube 12 is inserted. The block 110 further defines one or more coolant ports 82 which are in fluid communication with the retaining area 14. Coolant or other media 84 is injected into the retaining area 14 through the one or more ports 82. The media 84 not only acts to cool the tube 12 during the cutting process but also creates a positive pressure within the retaining area 14 to prevent dross, slag or other debris from entering the block 110.

Fluid media 84 may be any type of fluid such as including but not limited to: water, oils, water soluble cutting solutions, etc.

In some embodiments the block 110 defines a first or upstream end 114 and a second or downstream end 116. Adjacent to the first end 114 is positioned an upstream gland plate 120 in fluid communication with the retaining area 14. Adjacent to the second end 116 is positioned a downstream gland plate 124 that is also in fluid communication with the retaining area 14.

In some embodiments each gland plate 120 and 124 defines a labyrinth 122 and 126 respectively. Labyrinths 122 and 126 define one or more fluid pressure decreasing zones 130 which act to minimize loss of fluid media 84 injected into the retaining area 14.

When a fluid media 84 is injected into the retaining area 14, the media 84 forms a hydraulic bearing which retains the tube 12 within the retaining area as long as the media 84 injected into the retaining area, as indicated by arrow 84a far exceeds the amount of fluid media being lost through the gland plates 120 and 124. Though the hydraulic bearing created by the injection of fluid media 84 retains the tube 12 in the retaining area 14, the tube 12 is free to be rotated by any external means with the fluid media 84 providing a minimum of frictional interference.

The hydraulic bearing action of the embodiment shown in FIG. 10 provides a high centering accuracy due to the fact that the tube 12 is supported by equal pressure on equal surface areas of the tubing. By manipulating the fluid pressure, fluid viscosity, and the exposed surface area of the retaining area different process parameters may be attained.

Figure 11:
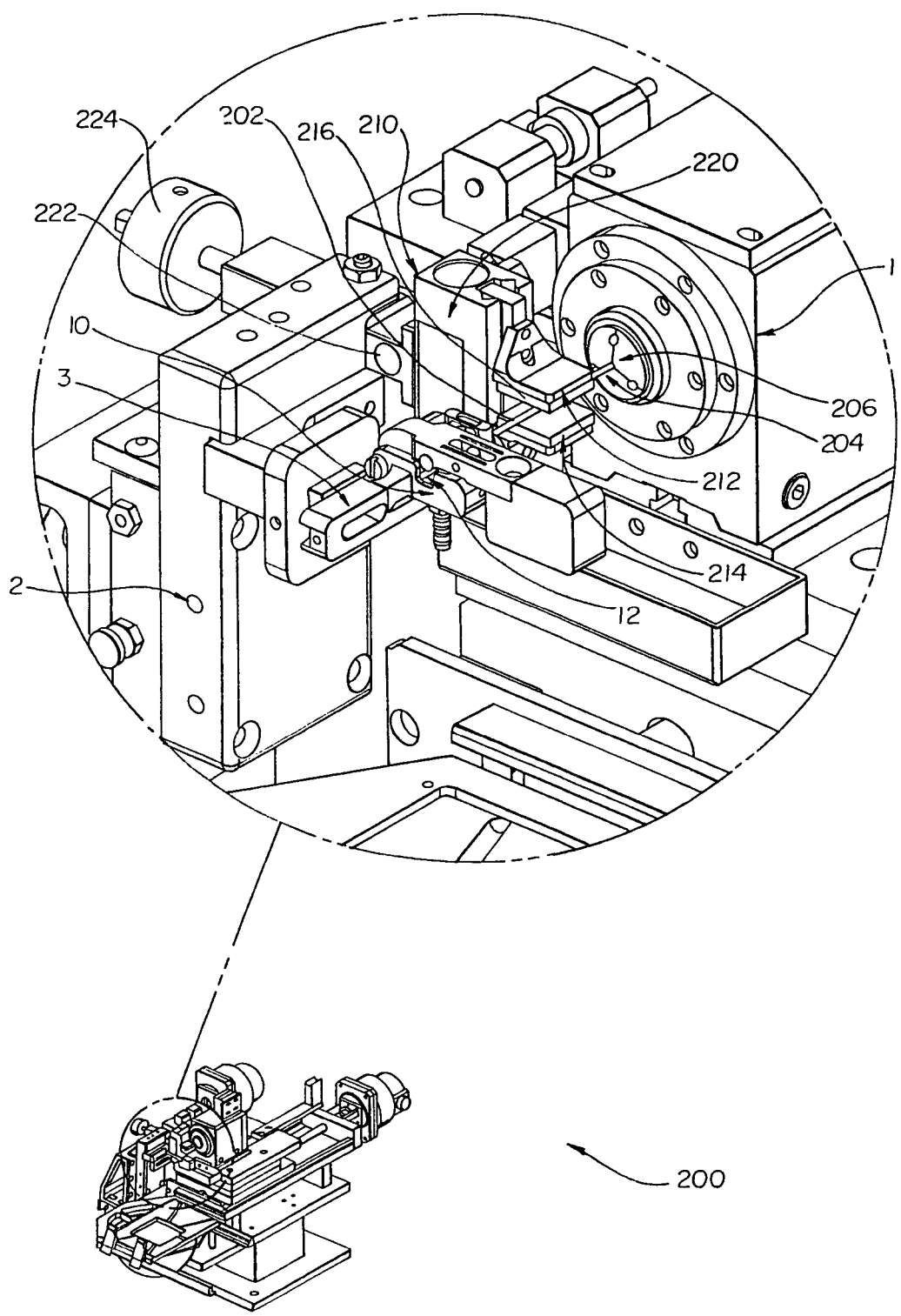
FIG. 11 is a partial perspective view of an embodiment of the invention comprising a tubular cutting system having a gripping mechanism and dynamic bushing.
Figure 12:
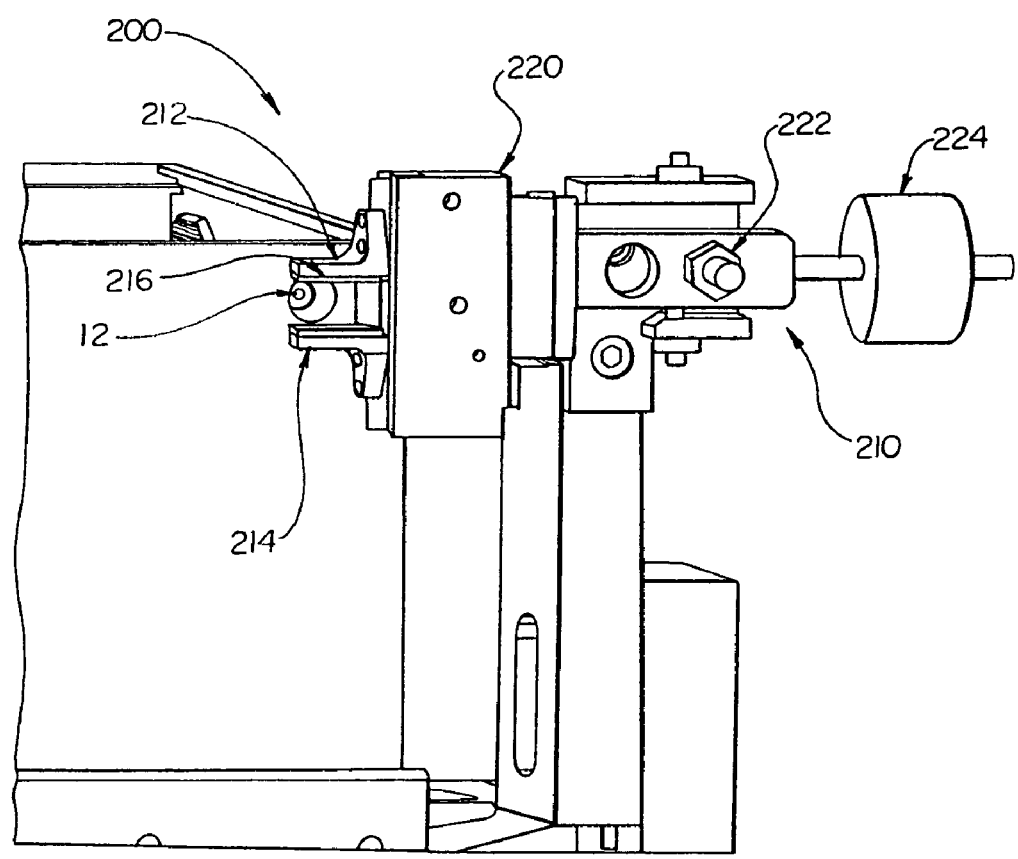
FIG. 12 is a partial perspective view of the embodiment shown in FIG. 11 wherein the gripping mechanism is illustrated in detail.

During the cutting of the tube 12 by the rotary assembly 200, such as is depicted in FIG. 11 a dynamic bushing assembly 10 constrains a distal portion 202 of the tube 12. While a distal portion 202 of the tube 12 is engaged by the dynamic bushing assembly 10, a more proximal portion 204 of the tube 12 is engaged by a rear collet 206 which provides further stability along the length of the tube 12 during the cutting process. After the cutting of a portion of the tube 12 is complete, the rear collet 206 is placed in an open configuration to release the tube 12, while the tube 12 remains engaged by the dynamic bushing 10 in accordance with any of the manners or configurations described herein. Before the tube 12 is released by the rear collet 206, a gripper mechanism 210 having at least two engagement members or moveable jaws 212 and 214, such as is shown in FIGS. 11 and 12, is actuated from an open position to a closed position wherein the jaws 212 and 214 are moved toward one another to grip the tube 12 while the tube is advanced within the assembly 200.

In at least one embodiment, jaws 212 and 214 are substantially rigid members that may be mounted parallel to one another or may be displaced at any angle desired. Each jaw 212 and 214 is provided with a gripping surface 216 which is constructed and arranged to engage the tube 12 so that the lateral movement of the tube is reduced or eliminated but the tube 12 is able to be advanced in a longitudinal direction without significant resistance. As such, the gripping surface 216 may be constructed of a variety of materials that may be relatively soft, hard, or a combination and/or composite thereof. In at least one embodiment the surface 216 is at least partially constructed of one or more relatively soft pads of natural and/or man-made materials such as wool, cotton, nylon, polyester, cloth, fiber, leather, etc. In some embodiments a relatively hard material may be used in conjunction with a relatively soft material to form the surface 216. For example, in at least one embodiment the surface 216 comprises a layer of relatively hard material and a layer of relatively soft material.

In at least one embodiment, the jaws 212 and 214 of the gripper mechanism 210 may be pneumatically actuated by a pneumatic source 220. In order to provide the mechanism 210 with a self-centering capability the mechanism 210 includes a counter weight 224 mounted opposite to the jaws 212 and 214. The entire assembly 210 is mounted on and about a low friction pivot member 222. The assembly is in substantially balanced gravitational equilibrium about the pivot member 222, which allows the jaws 214 and 214 to self-align on the center of the tube 12 and thus accommodate a wide range of tube 12 diameters without significant change over tasks or tooling changes.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A dynamic bushing assembly for preventing a tubular member from moving transverse to a longitudinal axis defined thereby but permitting the tube to be rotated about the longitudinal axis, the assembly comprising:
   a tube retention area, the tube retention area being defined at least partially defined by a crown member, the crown member defining an apex, the apex having at least one top guide member extending therefrom into the tube retention area, the tube retention area being further defined by a surface of a piston, the piston being moveable toward and away from the apex, the surface of the piston having at least two bottom guide members extending therefrom into the tube retention area, wherein at least one of the guide members comprises a roller ball.

2. The assembly of claim 1 further comprising a piston housing, the piston being moveably engaged to the piston housing and being moveable therethrough, the crown member being fixedly engaged to the piston housing.

3. The assembly of claim 2 further comprising a cradle, the cradle being supportively engaged to a portion of the piston housing.

4. The assembly of claim 3 further comprising an elevator mechanism, the elevator mechanism being engaged to at least a portion of the cradle, the elevator mechanism constructed and arranged to move the cradle in a vertically up and down direction.

5. The assembly of claim 1 wherein the at least one top guide comprises:
   a guide housing, at a first end of the guide housing the guide housing being engaged to the apex of the crown member, at a second end of the guide housing a roller ball is frictionally engaged to the guide housing, the roller ball being rotatable relative to the guide housing, the guide housing containing a biasing mechanism therein, the biasing mechanism exerting a predetermined biasing force on the roller ball in a direction toward the tube retaining area.

6. The assembly of claim 5 wherein the at least two bottom guides each comprise:
   a guide housing, at a first end of the guide housing, the guide housing being engaged to the surface of the piston, at a second end of the guide housing a roller ball is frictionally engaged to the guide housing, the roller ball being rotatable relative to the guide housing, the guide housing containing a biasing mechanism therein, the biasing mechanism, exerting a predetermined biasing force on the roller ball in a direction toward the tube retaining area.

7. The assembly of claim 6 wherein the biasing mechanism of the at least one top guide exerts a predetermined biasing force that is greater than the predetermined biasing force exerted by the biasing mechanism of each of the at least two bottom guides.

8. The assembly of claim 6 wherein the tube retaining area has a predetermined size, the size of the tube retaining area being reduced when the piston is moved toward the apex of the crown, the size of the tube retaining area being expanded when the piston is moved away from the apex of the crown.

9. The assembly of claim 8 further comprising a tubular member, the tubular member defining an external surface, the tubular member being positioned in the tube retaining area so that the roller ball of the at least one top guide contacts a point on the external surface of the tubular member and the roller ball of each of the at least two bottom guides contact a point on the external surface of the tubular member.

10. The assembly of claim 6 wherein each roller ball is at least partially constructed from a wear resistant material.

11. The assembly of claim 10 wherein the wear resistant material is selected from at least one member of the group consisting of: ceramic, crucible powder metal, tungsten carbide and any combination thereof.

12. The assembly of claim 6 wherein each biasing mechanism is selected from at least one member of the group consisting of: a spring, a pressurized fluid column, a hydraulic mechanism, and any combination thereof.

13. The assembly of claim 1 wherein the at least one top guide is moveably engaged to the crown.

14. The assembly of claim 1 wherein each of the at least two bottom guides are moveably engaged to the piston.

15. The assembly of claim 1 wherein the longitudinal axis has a substantially horizontal orientation.

* * * * *